(12) United States Patent
Pegross

(10) Patent No.: US 8,701,236 B2
(45) Date of Patent: Apr. 22, 2014

(54) ELECTRIC TOOTHBRUSH

(76) Inventor: Sherman Pegross, West Bloomfield, MI (US)

( * ) Notice: Subject to any disclaimer, the term of this patent is extended or adjusted under 35 U.S.C. 154(b) by 574 days.

(21) Appl. No.: 12/887,041

(22) Filed: Sep. 21, 2010

(65) Prior Publication Data

US 2011/0067187 A1     Mar. 24, 2011

Related U.S. Application Data

(60) Provisional application No. 61/244,104, filed on Sep. 21, 2009.

(51) Int. Cl.
*A46B 13/02*     (2006.01)

(52) U.S. Cl.
USPC ................................................. 15/23

(58) Field of Classification Search
USPC ................................................. 15/23
See application file for complete search history.

(56) References Cited

U.S. PATENT DOCUMENTS

| | | | |
|---|---|---|---|
| D48,666 S | 3/1916 | Boccia | |
| 2,044,344 A * | 6/1936 | Bagnall | 15/23 |
| 2,583,886 A * | 1/1952 | Schlegel | 15/23 |
| 3,621,505 A * | 11/1971 | Vocker | 15/23 |
| D232,278 S | 8/1974 | Gallo | |
| 3,859,684 A * | 1/1975 | Moskwinski | 15/23 |
| 4,845,796 A * | 7/1989 | Mosley | 15/23 |
| D385,703 S | 11/1997 | Etter | |
| 5,864,911 A * | 2/1999 | Arnoux et al. | 15/23 |
| D411,365 S | 6/1999 | Bauske, Sr. et al. | |
| 6,286,173 B1 | 9/2001 | Briones | |
| D473,381 S | 4/2003 | Matthews | |
| 2002/0002753 A1 | 1/2002 | Graham | |
| 2005/0144745 A1 * | 7/2005 | Russell | 15/23 |
| 2008/0028587 A1 | 2/2008 | Renault | |
| 2008/0034515 A1 | 2/2008 | Hilscher et al. | |
| 2008/0307591 A1 | 12/2008 | Farrell et al. | |

FOREIGN PATENT DOCUMENTS

| | | |
|---|---|---|
| DE | 34 38 700 A1 | 4/1986 |
| DE | 38 12 390 A1 | 8/1988 |
| DE | 38 19 249 A1 | 12/1988 |
| DE | 37 35 436 A1 | 5/1989 |

OTHER PUBLICATIONS http://www.animated-teeth.com/electric_toothbrushes/t3_sonic_toothbrushes.htm, "Sonic Toothbrush / Electric Toothbrush: The Soniccare Toothbrush," Apr. 14, 2009.

* cited by examiner

*Primary Examiner* — Randall Chin
(74) *Attorney, Agent, or Firm* — Carlson, Gaskey & Olds, P.C.

(57) ABSTRACT

An electric toothbrush includes a handle housing a motor and a drive shaft. A brushing member includes a base removably secured to the handle. The base supports at least two brushes, each configured to rotate about separate axes, and at least one input shaft operatively coupling the drive shaft to the brushes. In one example, the handle includes an articulateable joint operatively connected to the brushing member and configured to permit the axes to cant relative to the handle.

17 Claims, 4 Drawing Sheets

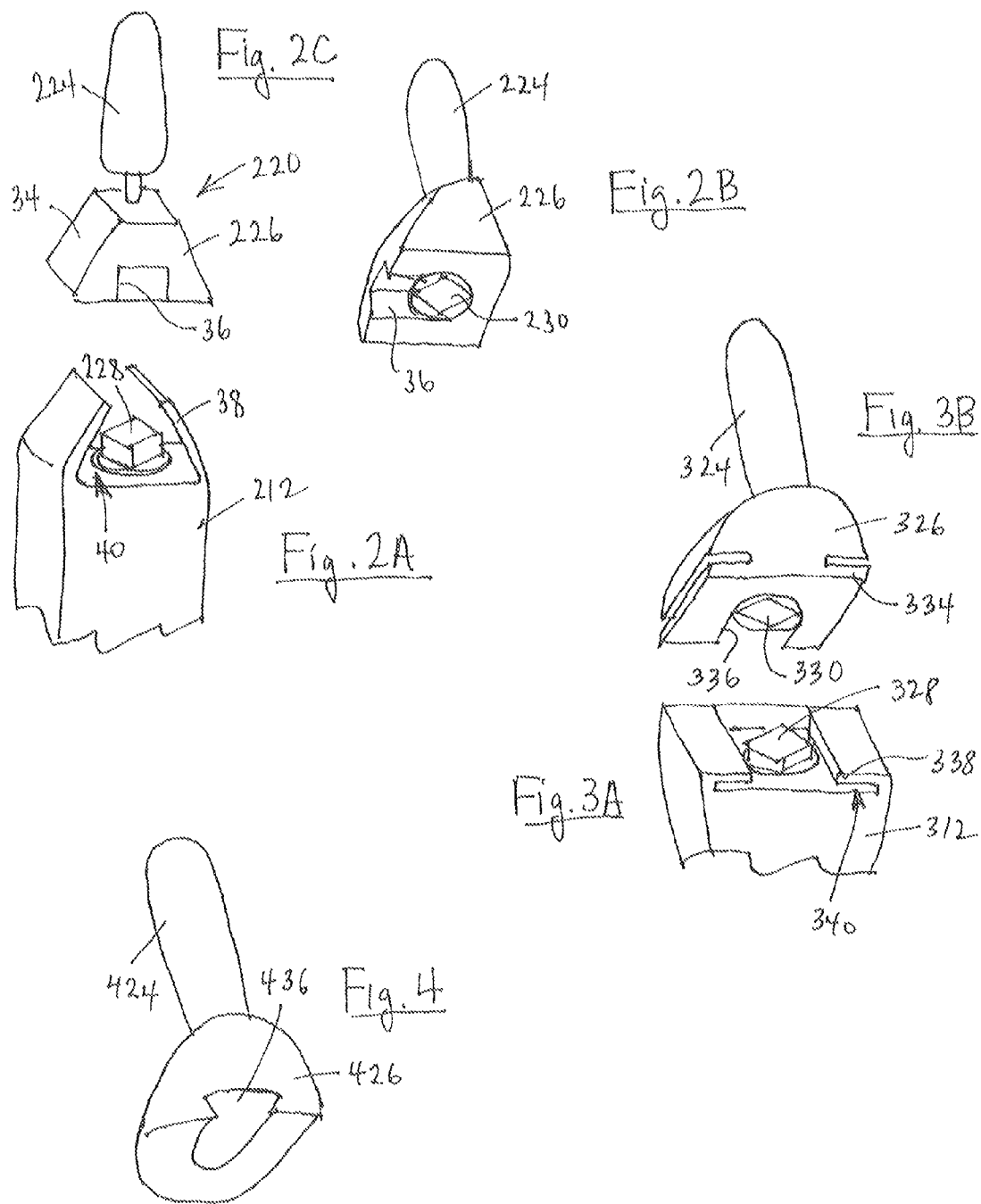

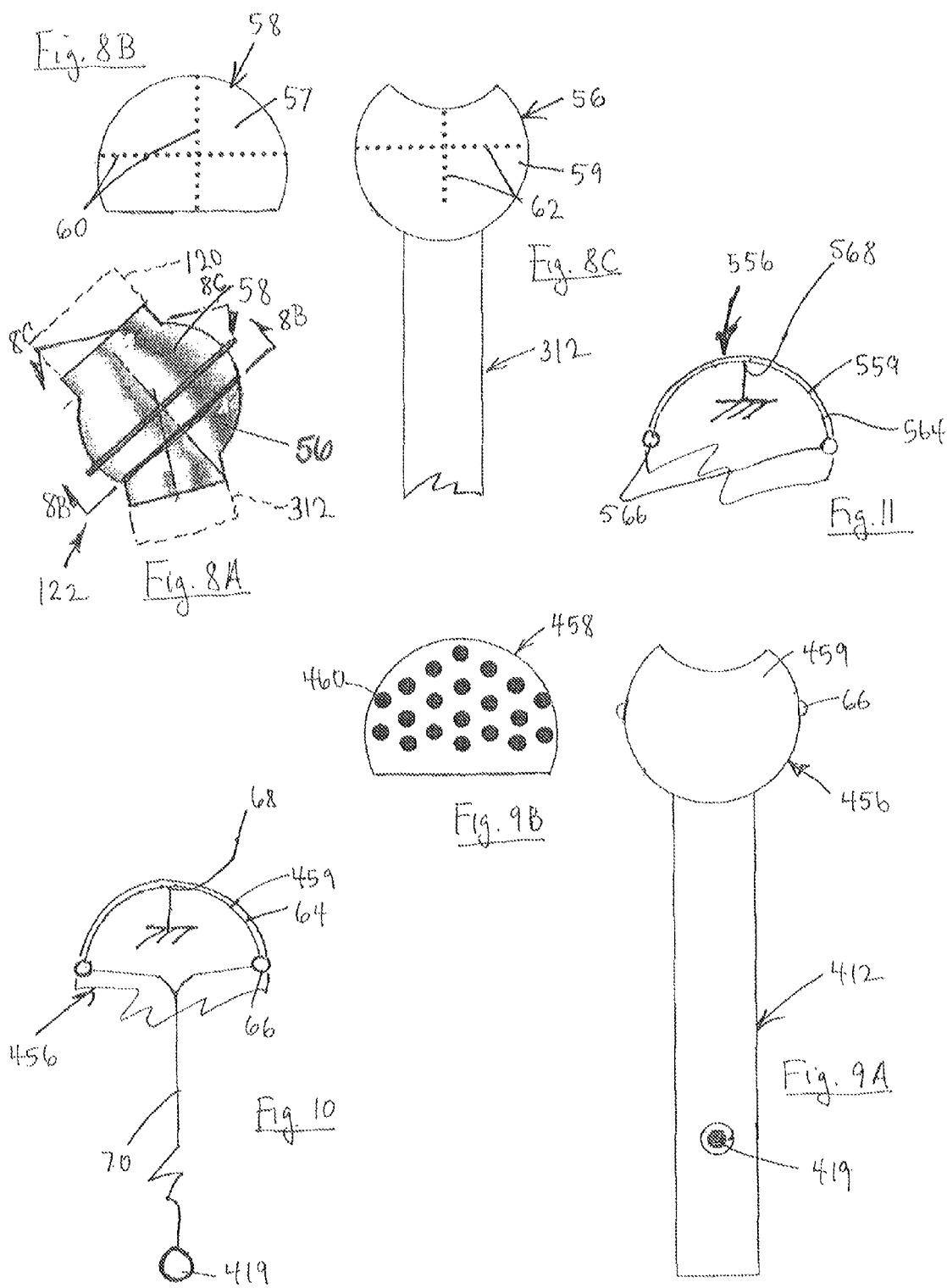

ELECTRIC TOOTHBRUSH

This application claims priority to U.S. Provisional Application No. 61/244,104, filed on Sep. 21, 2009.

BACKGROUND

Electric toothbrushes are available in a variety of configurations. The most common configuration is a handle housing a motor and a single drive element. A brushing member having a single brush is removably secured to the handle and is operatively driven by the drive element.

Another configuration includes a pair of brushes rotationally driven in opposite directions, as disclosed in DE 373546 to Linde. Each brush is separately inserted into the handle and coupled to the drive element. As a result, a greater number of parts must be manipulated by the user, making brush changes more complicated. Moreover, the rotational axes of the brushes are fixed relative to the handle, which may make full engagement between the brushes and the user's teeth more difficult.

SUMMARY

An electric toothbrush includes a handle housing a motor and a drive shaft. A brushing member includes a base removably secured to the handle. The base supports at least two brushes, each configured to rotate about separate axes, and at least one input shaft operatively coupling the drive shaft to the brushes. In one example, the handle includes an articulateable joint operatively connected to the brushing member and configured to permit the axes to cant relative to the handle.

BRIEF DESCRIPTION OF THE DRAWINGS

FIGS. 2A-2C illustrate another example removable brushing member configuration.

FIGS. 3A-3B illustrate another example removable brushing member configuration.

FIG. 4 illustrates yet another removable brushing member.

FIGS. 8A-8C illustrate an example articulateable joint supporting the brushing member relative to the handle.

FIG. 9A-9B illustrates another example articulateable joint.

FIG. 10 illustrates an example lock for the articulateable joint shown in FIG. 9A.

FIG. 11 illustrates another example lock for the articulateable joint illustrated in FIG. 9A.

DETAILED DESCRIPTION

Figure 1A:
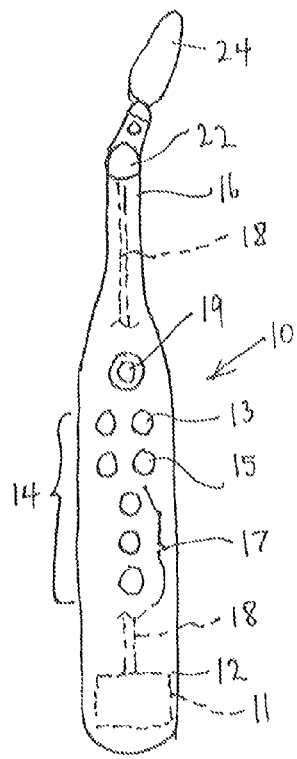
FIG. 1A is a schematic view of an example electric toothbrush.
Figure 1B:
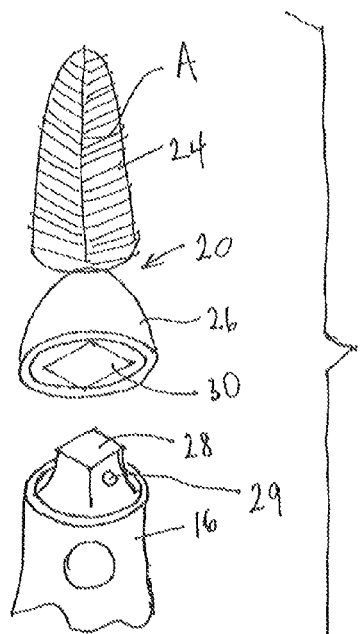
FIG. 1B is an enlarged exploded perspective view of a removable brushing member shown in FIG. 1A.

Referring to FIGS. 1A and 1B, an electric toothbrush 10 includes a handle 12 having controls 14. Like numerals are used throughout this disclosure to indicate like elements. The controls 14 may provide various features, for example, on/off (button 13), spin direction (clockwise/counterclockwise) of brushes (button 15), speed control (e.g., buttons 17 providing high, medium, low speeds), and/or brush oscillations (e.g., brushes spinning in the opposite direction every two seconds).

An end 16 of the handle 12 removably supports a brushing member 20 at a joint 22. The brushing member 20 includes a base 26 that supports the brush 24 for rotation about an axis A. The handle 12 houses a driving element such as a driveshaft 18 that rotates a drive lug 28, which cooperates with a driven lug 30 carried by the base 26. The driveshaft 18 is driven by a motor 11.

A release button 19 is used to selectively lock the brushing member 20 in a position relative to the handle 12 using a spring-loaded lock 29, which gives the base 26 a firm fit to the drive lug 28. In one example, the release button 19 simply selectively secures the brushing member 20 to the handle 12. In another example, the release button 19 retains the brushing member 20 in a desired canted position relative to the handle 12, as illustrated in FIG. 8A.

Figure 1C:
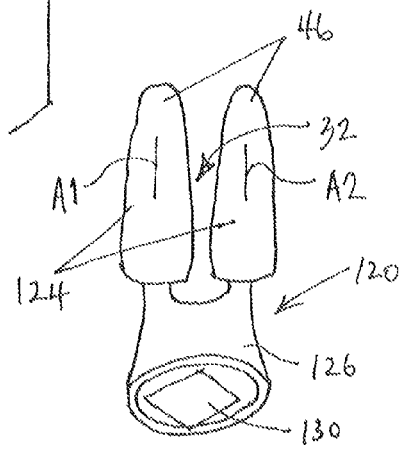
FIG. 1C is a perspective view of another example removable brushing member.

A dual brush arrangement 120 is illustrated in FIG. 1C. The dual brush arrangement 120 includes a pair of brushes 124 supported on a base 126 for rotation about separate axes A1, A2 that are generally parallel to one another. The brushes 124 are driven by driven lug 130. A gap 32 is provided between the brushes 124 to accommodate teeth of the user such that both sides of the teeth can be simultaneously brushed by the electric toothbrush 10. It should be understood, however, that a gap 32 need not be provided and that the brushes 124 may be arranged in close proximity to one another such that they overlap slightly with one another. In the example, the brushes 124 rotate in opposite directions, i.e., one brush rotates counterclockwise and the other brush rotates clockwise.

Figure 1D:
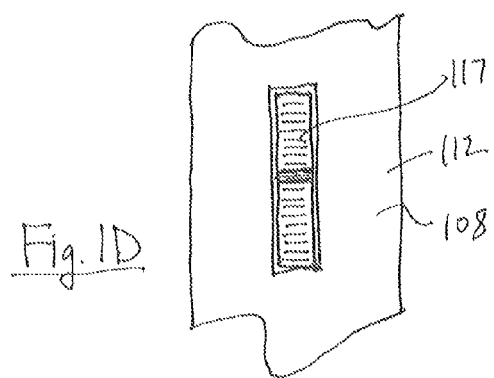
FIG. 1D is an enlarged plane view of an example electric toothbrush control.
Figure 1E:
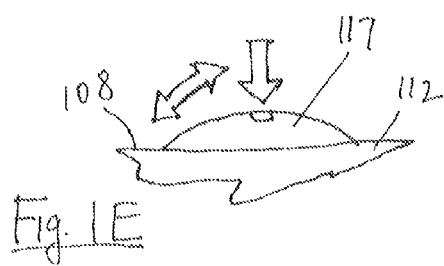
FIG. 1E is a side elevational view of the electric toothbrush control illustrated in FIG. 1D.

Referring to FIGS. 1D and 1E, the handle 112 includes an input switch 117 in communication with the motor 11 and configured to be slidable relative to an exterior 108 in first and second opposing directions (hollow double arrow in FIG. 1E) and depressible in a third direction (hollow single arrow in FIG. 1E) transverse to the first and second directions. In the example, the input switch 117 is a wheel.

In one example, the first and second directions respectively correspond to first and second opposing rotational directions of the brushes 124 about the axes A1, A2, and the third direction corresponds to an on/off mode. In another example, a sliding distance of the input switch 117 in the first and second direction corresponds to a speed. The speed increases with a corresponding increase in distance from a central input switch position (shown by the notch in the wheel in FIGS. 1D and 1E). The third direction may correspond to a pulsate mode.

FIGS. 2A-4 illustrate various configurations for removably securing the base of the brushing member to the handle 212, 312. Referring to FIGS. 2A-2C, the base 226 includes a recess 36 to accommodate the drive lug 228 as the base 226 is slidably received on an end of the handle 212. The base 226 and handle 212 include complementary features that interlock with one another to maintain the drive lug 228 and driven lug 230 into engagement with one another during operation of the electric toothbrush 10. In one example, the base 226 includes an exterior surface 34 having a shape (generally triangular, for example) that is complementary to a shape provided by retaining elements 38 on the handle 212. In operation, the base 226 is aligned with a slot 40 such that the recess 36 is facing the drive lug 28. The base 126 is slid into the slot 40 until the drive lug 228 engages the driven lug 230.

The driven lug 230 may include an open end that is aligned with the drive lug 228 during insertion of the base 226 into the handle 212. Alternatively, the release button 19 (FIG. 1A) is configured to retract the drive lug 228, obviating the need for the recess 36 and open end on the driven lug 230.

Another example configuration is illustrated in FIGS. 3A-3B. The base 326 includes opposing legs 334 adjacent slots that receive complementary retaining elements 338. The legs 334 are received in corresponding slots 340 with the base 326 installed into the handle 312. The base 326 supports brush 324. The drive lug 328 and driven lug 330 cooperate with one another with the base 326 installed on the handle 312. The recess 336 accommodates the drive lug 328 during installation.

Another example base 426 is illustrated in FIG. 4. The base 426 includes another configuration of a slot 436, which cooperates with a correspondingly shaped feature on the handle. The base 426 supports a brush 424.

Figure 5:
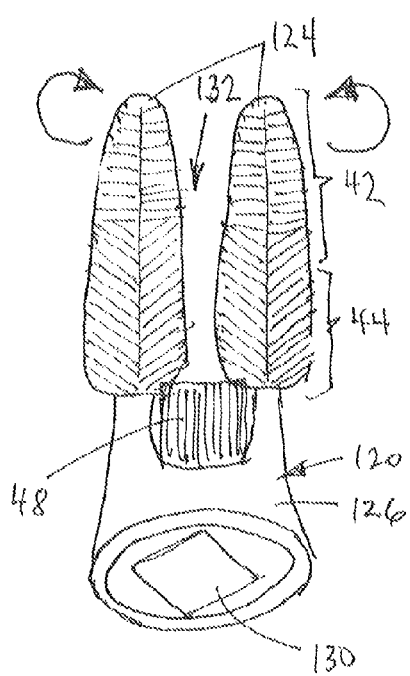
FIG. 5 illustrates a removable brushing member similar to that shown in FIG. 1C with an additional fixed brush.

Example brushes are depicted in FIG. 5. An arrangement 120 having a pair of brushes 124 is provided for relative rotation with respect to one another via the driven lug 130. The brushes 124 each include at least two sets of bristles 42, 44 that are oriented differently than one another. In one example, the brush 124 includes a first set of bristles 42 that extends generally radially outwardly (almost perpendicularly) from the brushes' axis of rotation. A second set of bristles 44 extends from the axis of rotation at a more acute angle than the first set of the bristles 42. In this manner, the set of bristles located near a terminal end 46 (FIG. 1C) are more perpendicular to the user's teeth than the set of bristles in closer proximity to the handle, enabling the second set of bristles 44 to better clean the generally horizontal portion of the user's teeth.

A fixed brush 48 is supported on the base 126 between the brushes 124 beneath the gap 132. In this manner, the fixed brush 48 engages the generally horizontal portion of a tooth while the spaced apart brushes 124 engage the lateral surfaces of the tooth. The fixed brush 48 may also be movable. The three brushes 124, 148 cooperate to simultaneously brush all sides of a tooth, which greatly reduces brushing time and increases efficiency.

Figure 7:
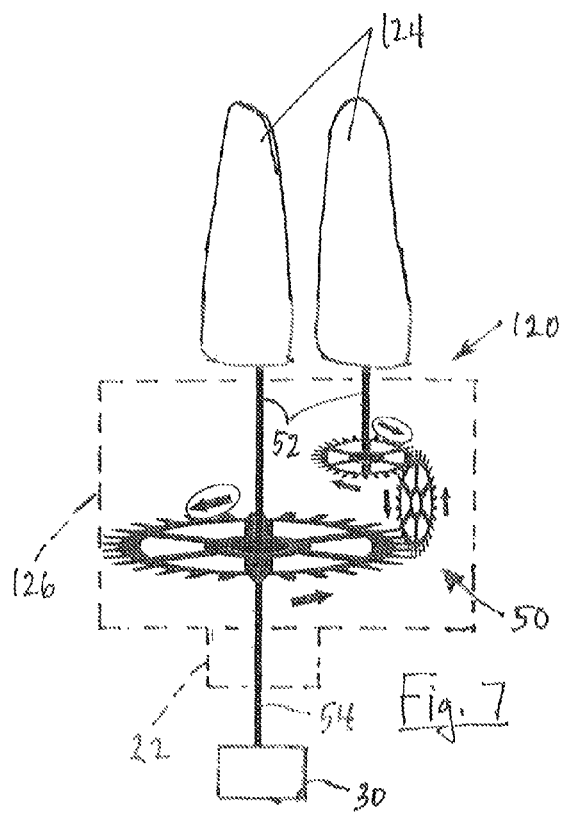
FIG. 7 illustrates another example multi-brush drive train.

A dual brush arrangement 120 is schematically illustrated in more detail in FIG. 7. The dual brush arrangement 120 includes a base 126 housing a drive train 50. The drive train 50 may be configured differently than illustrated, if desired. The base 26 supports an input shaft 54 connected to the driven lug 30, which may be provided at the joint 22. The input shaft 54 is coupled to the drive train 50 to rotationally drive output shafts 52 connected to the brushes 24. In the example shown, the drive train 50 is configured to provide opposite rotation of the brushes 24.

Figure 6:
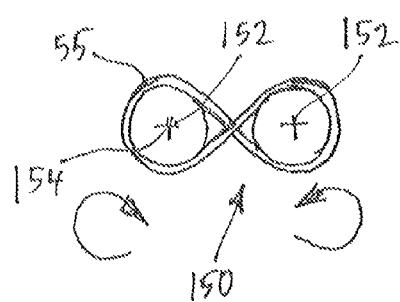
FIG. 6 schematically illustrates an example multi-brush drive train.

Another example is drive train 150 is shown in FIG. 6 in which first members are driven by a second member 55 to achieve opposite rotation of the output shafts 152. The input shaft 154 may be coaxial with one of the output shafts 152.

Various joints are illustrated in FIGS. 8A-11. One example joint 122 (FIGS. 8A-8C) includes a cup 58 (458 in FIG. 9B) supported on a ball 56 (456 and 556 in FIGS. 10 and 11, respectively) in a snap-fit relationship.

The cup 58 includes an inner surface 57 having multiple protrusions 60. In one example, the protrusions 60 are arranged along intersecting horizontal and vertical planes. The ball 56 includes corresponding recesses 62 on an outer surface 59 (459 and 559 in FIGS. 10 and 11, respectively) complementary in shape to the protrusions 60 and also arranged in intersecting horizontal and vertical planes. The protrusions and recesses 60, 62 provide a "home" position in which the brushing member 120 is locked relative to the handle 312 in a particular orientation, for example, with the brush or brushes extending longitudinally from the handle 312. Applying a lateral force to the brushing member 120 relative to the handle 312 unlocks the cup 58 from the ball 56 enabling the brushing member 120 to swivel and/or cant relative to the handle 312, which enables the brushing member 120 to be positioned in a more convenient orientation with respect to the handle 312 providing easier access to the user's teeth. The protrusions and recesses may be provided over a greater area of the ball and cup, if desired.

A similar arrangement is illustrated in FIGS. 9A-11. The joint includes a ball 456 having movable balls 66 (566 in FIG. 11) that are biased outward from the ball 456 by a spring element 64 (564 in FIG. 11). The spring element 64 is affixed to the ball 456 by a fixing element 68 (568 in FIG. 11). The spring element 64 urges the balls 66 into engagement with complementary shaped recesses 460 in the cup 458. The cup 458, which is shown in FIG. 9B, includes multiple recesses 460 arranged on its inner surface 157 in a pattern similar to that of a golf ball surface, which enables the cup 458 to be locked relative to the balls 66 in a great number of positions. Referring to FIGS. 9A and 10, the balls 66 can be retracted by the release button 419 on the handle 412, which is interconnected to the balls 66 by a connection 70.

Although example embodiments have been disclosed, a worker of ordinary skill in this art would recognize that certain modifications would come within the scope of the following claims.

What is claimed is:

1. An electric toothbrush comprising:
a handle housing a motor and a drive shaft;
a brushing member including a base removably secured to the handle, the base supporting at least two brushes each configured to rotate about separate axes, and at least one input shaft operatively coupling the drive shaft to the brushes; and
wherein the handle includes an articulateable joint operatively connected to the brushing member and configured to permit the axes to cant relative to the handle.

2. The electric toothbrush according to claim 1, wherein the brushing member has a single input shaft coupled to the drive shaft, the input shaft operatively coupled to at least two output shafts respectively connected to the at least two brushes.

3. The electric toothbrush according to claim 1, wherein another brush is affixed to the base between the at least two brushes, with the other brush including bristles extending generally in the direction of the axes.

4. The electric toothbrush according to claim 1, wherein the handle includes a first feature and the base includes a second feature interlocking with the first feature in a mounted position, the first and second features slideable relative to one another from an unmounted position to the mounted position in a direction transverse to the axes.

5. The electric toothbrush according to claim 4, wherein the handle includes a drive lug configured to be operatively driven by the motor, the base includes a slot configured to accommodate the drive lug when moving the base between unmounted and mounted positions.

6. The electric toothbrush according to claim 1, wherein the articulateable joint includes a ball and cup arrangement with at least one detent provided between the ball and cup configured to maintain a desired orientation.

7. The electric toothbrush according to claim 6, wherein the at least one detent includes a spring load configured to bias the detent into engagement with the cup.

8. The electric toothbrush according to claim 7, wherein the handle includes a release button, the button operatively connected to the detent to reduce the spring load.

9. An electric toothbrush comprising:
a handle housing a motor and a drive shaft;
a brushing member including a base removably secured to the handle, the base supporting at least two brushes each configured to rotate about separate axes, and at least one input shaft operatively coupling the drive shaft to the brushes; and
wherein the handle includes a release button and a retractable lock, the retractable lock cooperating with the base in a mounted position to selectively retain the base on the handle.

10. An electric toothbrush comprising:
a handle housing a motor and a drive shaft;
a brushing member including a base removably secured to the handle, the base supporting at least two brushes each configured to rotate about separate axes, and at least one input shaft operatively coupling the drive shaft to the brushes; and
wherein the handle includes an input switch in communication with the motor and configured to be slidable relative to an exterior in first and second opposing directions and depressible in a third direction transverse to the first and second directions.

11. The electric toothbrush according to claim 10, wherein the input switch is a wheel.

12. The electric toothbrush according to claim 10, wherein the first and second directions respectively correspond to first and second opposing rotational directions of the brushes about the axes, and the third direction corresponds to an on/off mode.

13. An electric toothbrush comprising:
a handle housing a motor and a drive shaft;
a brushing member including a base removably secured to the handle, the base supporting at least two brushes each configured to rotate about separate axes, and at least one input shaft operatively coupling the drive shaft to the brushes; and
wherein the handle includes an input switch in communication with the motor and configured to be slidable relative to an exterior in first and second opposing directions and depressible in a third direction transverse to the first and second directions, and a sliding distance in the first and second directions corresponds to a speed, the speed configured to increase with a corresponding increase in distance from a central input switch position.

14. An electric toothbrush comprising:
a handle housing a motor and a drive shaft;
a brushing member including a base removably secured to the handle, the base supporting at least two brushes each configured to rotate about separate axes, and at least one input shaft operatively coupling the drive shaft to the brushes; and
wherein the handle includes an input switch in communication with the motor and configured to be slidable relative to an exterior in first and second opposing directions and depressible in a third direction transverse to the first and second directions, and the third direction corresponds to a pulsate mode.

15. A brushing member comprising:
a base supporting at least two brushes, each configured to rotate about separate axes provided by output shafts; and
a driven lug supported by the base and including an interlocking attachment feature configured to cooperate with a spring-loaded lock that removably secures the base to an electric toothbrush handle.

16. The brushing member according to claim 15, wherein the base includes at least one input shaft, and a drive train is operatively coupled to the input shaft and the output shaft, and the drive train is configured to provide rotation of the brushes in opposite rotational directions.

17. The brushing member according to claim 15, another brush is affixed to the base between the at least two brushes.

* * * * *